United States Patent
Rehberger (12) 
(10) Patent No.: US 6,221,650 B1
(45) Date of Patent: *Apr. 24, 2001

(54) **WASTE TREATMENT WITH A COMBINATION OF DENITRIFYING *PROPIONIBACTERIUM ACIDIPROPIONICI* AND PROTEASE-PRODUCING BACILLUS**

(75) Inventor: Thomas G. Rehberger, Wauwatosa, WI (US)

(73) Assignee: AgTech Products, Inc., Waukesha, WI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/918,778

(22) Filed: Aug. 25, 1997

(51) Int. Cl.$^7$ .............................. C12N 1/20; C02F 3/00; B09B 3/00

(52) U.S. Cl. .................. 435/252.4; 210/601; 435/252.1; 435/252.5; 435/262.5; 435/822; 435/832; 435/836; 435/839

(58) Field of Search ..................................... 435/220, 221, 435/252.1, 242.5, 822, 832, 836, 839; 210/601

(56) References Cited

U.S. PATENT DOCUMENTS

| | | | |
|---|---|---|---|
| 5,464,766 | * | 11/1995 | Bruno .................................... 435/187 |
| 5,945,333 | * | 8/1999 | Rehberger ............................. 435/628 |
| 6,120,810 | * | 9/2000 | Rehberger et al. ..................... 426/61 |

OTHER PUBLICATIONS

Loveland Industries, Inc. Specification Sheet, "Micro Treat "NR" Maintenance Formulation", pp. 1 and 2, Revised Aug. 7, 1996.

Loveland Industries, Inc., "Micro Treat "NR" Specific Bacteria that Enhance the Natural Process of Waste Digestion to Reduce Excess Nitrogen, Solids and Odors in Livestock Waste", Jan., 1997.

Schmidt et al, Agricultural Engineering Department, University, University of Minnesota, "Manure Management: Practices for the Minnesota Pork Industry", pp. 1–32, 1994.

Council for Agricultural Science and Technology, Waste Management and Utilization in Food Production and Processing, CAST, pp. 42–54, Oct. 1995.

Loveland Industries, Inc. Technical Bulletin, "Micro Treat "NR" Swine Lagoon Study North Carolina Field Trial", pp. 1 and 2, Revised Aug. 4, 1997.

"Big Lagoons and the "N factor"", Feedstuffs, p. 19, Feb. 17, 1997.

"Landowners seek revoking of PSF facility permits", Feedstuffs, pp. 5 and 23, Aug. 4, 1997.

* cited by examiner

Primary Examiner—David M. Naff
(74) Attorney, Agent, or Firm—Andrus, Sceales, Starke & Sawall, LLP (57) ABSTRACT

Waste such as livestock waste is treated with a combination of protease-producing bacteria and denitrifying bacteria that synergistically reduce nitrogen concentration, and further reduce noxious odors associated with anaerobic decomposition. The protease-producing bacteria break down complex proteins in the waste which enables ammonification by other naturally occurring microorganisms already present in the waste. The denitrifying bacteria then convert products of ammonification such as nitrates and nitrites to nitrogen gas which is released into the atmosphere. The protease-producing bacteria produce neutral and alkaline proteases, and are preferably from the genus Bacillus and include *Bacillus subtilis*, *Bacillus licheniformis* and *Bacillus amyloliquefaciens* provided at a level of at least approximately $4.5 \times 10^4$ CFU/ml. The denitrifying bacteria produce nitrate reductase, nitrite reductase and nitrous oxide reductase, and is preferably *Propionibacterium acidipropionici* strain P5 (ATCC 55467) provided at a level of at least approximately $3.0 \times 10^4$ CFU/ml. The protease-producing bacteria and denitrifying bacteria are added to waste as a composition containing both bacteria, or the protease-producing bacteria is added first followed by addition of the denitrifying bacteria. In addition to both bacteria, the composition contains a water soluble carrier such as whey or maltodextrin, and a moisture binding agent such as balith.

23 Claims, 3 Drawing Sheets

FIG. 3

WASTE TREATMENT WITH A COMBINATION OF DENITRIFYING *PROPIONIBACTERIUM ACIDIPROPIONICI* AND PROTEASE-PRODUCING BACILLUS

CROSS-REFERENCE TO REBATED APPLICATIONS

N/A

STATEMENT REGARDING FEDERALLY SPONSORED RESEARCH OR DEVELOPMENT

N/A

BACKGROUND OF THE INVENTION

Nitrogen is a vital chemical element found in all living organisms, constitutes 78% of the air we breath, and is an essential plant nutrient. However, excess nitrogen such as $NH_3$, nitrite and nitrate, in soil or water causes serious problems.

Some microorganisms are able to reduce nitrate and nitrite to nitrogen gas in a process called "denitrification". This results in nitrogen actually being removed from soil and water, thereby releasing $N_2$ gas into the air. Denitrification maintains the potability of fresh waters and maintains productivity of land masses due to the fact that high concentrations of nitrate ions are toxic. This is especially true when the land mass has an excessive amount of organic matter present, such as areas where manure is generated from livestock.

Denitrification is absolutely vital to the continued availability of combined nitrogen on the land masses of the earth. Nitrates in topsoil are used by plants as an essential nutrient. However, nitrates are also soluble in water and can leach through the soil and into the ground water or runoff across the soil surface to lakes and streams, depending on the soil texture, permeability and land topography. The potential for leaching or runoff from soil increases when the amount of nitrogen applied to the crop lands exceeds the actual needs of the crop itself. Without denitrification, the earth's supply of nitrogen, would eventually accumulate in the oceans precluding life on the land masses, except for a fringe near the oceans.

Excessive nitrogen in the environment from various sources, such as animal waste, and the process of denitrification are issues of growing concern and interest. Manure management plays a critical role in determining how nitrates impact crop production and environmental pollution. This is especially true since the current trend in the livestock industry is moving away from small farms having 100 head or less of livestock, toward the large mega-producers which have thousands of livestock. This growing trend toward these enormous "mega farms", which raise thousands of livestock per year, result in the daunting problem of handling and disposal of massive amounts of manure. This puts a serious demand on the land the livestock is raised on as well as surrounding lands and nearby water supplies. Megafarms typically raise large numbers of livestock in very close quarters resulting in dense manure generation on a relatively small plot of land. For example, swine production in Minnesota alone generate approximately 11 million tons of manure containing 73,000 tons of nitrogen annually, and Minnesota is not even the top swine producing state.

Manure and other livestock waste has the potential to be either a valuable resource or a major pollutant, depending on its management. When not treated or improperly handled, manure nutrients, primarily nitrogen, are potential pollutants of air and water. Thus, manure management in the livestock industry has recently received a great deal of attention. Focus on this issue has occurred for several reasons. The major reason is recent advancements in science have clarified the connection between manure and pollution. In some situations, declining water quality has been directly linked to poor manure management.

Ground water contamination resulting from nitrate leaching and runoff has serious ramifications. Nitrate contaminated water poses a health risk when it is consumed by humans or animals. Health problems associated with nitrate result primarily after the nitrates enter the body and are converted by bacteria to nitrite. High nitrite levels cause a condition known as methemoglobinemia. Methemoglobinemia, also known as "blue baby syndrome", is due to the conversion of nitrate to nitrite by nitrate reducing bacteria in the gastrointestinal tract. Hemoglobin is converted to a brown pigment, methemoglobin, following oxidation by nitrite of $Fe^{2+}$ in hemoglobin to $Fe^{3+}$. Since methemoglobin is incapable of binding molecular oxygen, the ultimate result is suffocation. Therefore, high levels of nitrogen in areas in which ground water makes up a large portion of the drinking water is a real and valid danger.

Further, additions of raw or semi-treated manure to a lake or stream will significantly degrade water quality. Manure additions increase the nitrogen and organic matter content of the lakes and streams contributing to excessive algae and aquatic plant growth. This growth has a high oxygen demand resulting in gradual depletion of the water's oxygen supply. This algae and plant bloom adversely affects fish and other aquatic life and has a negative impact on the beneficial use of water resources for drinking or recreation. If oxygen concentrations fall below a critical level, fish and other aquatic species die in massive numbers.

Not only are there human health concerns and danger to area aquatic species, but odor also presents a major problem in raising livestock. Odor issues often create tension between livestock producers and neighbors or entire communities. Because odors are produced during the anaerobic decomposition of manure, the surest way to decrease odors is to provide oxygen to the manure via aeration. However, aeration is not practical, is very expensive and necessitates high energy requirements.

Focus on manure management is the result of the public's increasing environmental concerns. For a majority of the public, the words "manure" and "pollution" have become synonymous. Due to the actual and perceived problems with manure, the public is demanding livestock producers have accountability in regard to manure handling and treatment. In fact, there are an increasing number of federal lawsuits filed against livestock producers claiming that the producers have violated the U.S. Clean Water Act, Clean Air Act and National Pollution Discharge Elimination System Permit Programs. Therefore, manure management and treatment is becoming a major factor in local, national and international livestock production. It is clear that livestock producers must effectively treat their manure and other waste products in order to avoid the aforementioned problems, and possibly even expensive and lengthy lawsuits.

There are many treatment systems currently utilized to handle the massive amounts of manure generated, including liquid-solid separation, composting, oxygen ditches, physical removal, digging deeper lagoons and the like. However, there are many problems and drawbacks associated with each and, on the whole, treatment systems are not typically cost effective.

Liquid-solid separation systems, such as settling basins and mechanical separators, provide a means of separating nutrients from the waste stream. However, the separation of nutrients requires relatively large mechanical separators which can be quite costly and require substantial amounts of energy.

Composting reduces and stabilizes the organic matter, but can require quite a large amount of time in order to properly compost the manure into a uniform, dry and odorless soil conditioner.

Oxidation ditches stabilize and reduce the organic matter in the waste material. However, these systems are relatively uncommon and typically uneconomical due to their high energy demands.

Some mega-producers have resorted to building miles and miles of pipe line in order to physically transport waste material to available land some distance from the farm itself. However, this is a cumbersome method of handling manure as well as an expensive one. Further, neighboring communities are threatened by pipe bursts or leaks.

Other producers have resorted to digging deeper lagoons, as much as 20–25 feet deep, as opposed to the standard 8–10 feet deep lagoon, in order to store waste material. However, the increase in depth dramatically decreases the surface-to-volume ratio, resulting in exceedingly high nitrogen levels.

What is desperately needed in the livestock industry is a waste treatment to reduce harmful nitrogen levels which is economically feasible, technically viable, easy to use and environmentally sound.

The present invention utilizes the natural process of denitrification to reduce nitrogen levels and is less expensive than the prior art treatment methods. Further, this invention does not require long periods of time before it effectively begins to reduce nitrogen levels. This invention also does not require large amounts of energy or specialized equipment, like some of the prior art treatment methods mentioned above. Further, the present invention is simple, easy to use and does not utilize potentially harmful or dangerous chemicals.

Specifically, this novel composition denitrifies harmful nitrogen compounds to nitrogen gasses and is thereby able to significantly reduce nitrogen levels in areas containing large amounts of nitrogen-containing biological waste.

BRIEF SUMMARY OF THE INVENTION

The present invention is a novel composition which contains a unique combination of bacterial strains capable of reducing nitrates and other nitrogen compounds to nitrogen gasses under anaerobic conditions. The enzymes produced by the bacteria present in the inventive composition are able to decrease total nitrogen concentration in soil or water caused by, for example, livestock waste. The nitrogen compounds reduced include organic nitrogen, ammonia, nitrates and nitrites.

Specifically, the novel composition consists of a unique combination of protease-producing bacteria and denitriying bacteria which synergistically reduce nitrogen concentrations in livestock waste. The protease-producing bacteria are able to break down complex proteins present in the manure which thereby enables ammonification by other naturally occurring microorganisms already present in the waste material. The denitrifying bacteria are then able to convert the products of ammonification, specifically nitrates and especially nitrites, to nitrogen gas, which is subsequently released into the atmosphere.

The protease-producing bacteria produce neutral and alkaline proteases and are preferably from the genus Bacillus. The Bacillus are a combination is *Bacillus subtilis, Bacillts licheniformis* and *Bacillus amyloliquefaciens*. The denitrifying bacteria produce nitrate reductase, nitrite reductase and nitrous oxide reductase and are preferably *Propionibacterium acidipropionici* strain P5. Without this unique blend of both types of bacteria, denitrification of the waste could not occur at any significant level.

DETAILED DESCRIPTION OF THE INVENTION

The majority of the nitrogen material present in animal waste is organic. Livestock manure contains various chemical forms of nitrogen, most in the organic form (proteins, amino acids, and urea) and some in the inorganic form (nitrates, ammonium, and ammonia). Relative amounts of a nitrogen in each form depend on several factors: temperature, moisture, pH, nitrogen concentration, oxygen concentration and carbon:nitrogen ratio. Changes in any of these factors affect both the total amount of nitrogen remaining in the manure and the chemical form of the nitrogen and, therefore, affect treatment and management practices.

There are several steps which must occur in order for denitrification of animal waste to eventually occur. Prior to denitrification, the organic nitrogen must be converted to inorganic nitrogen. Microorganisms in manure are not effective at converting organic nitrogen, usually in the form of large complex proteins, into inorganic nitrogen. Unfortunately, a large percentage of the nitrogen present in manure is in the form of these complex protein molecules. Therefore, denitrification cannot occur unless these complex proteins are first broken down.

A major hurdle which is overcome by the present invention is the breakdown of complex nitrogen molecules to simpler molecules, thereby enabling the eventual denitrification of the waste. Without this specific combination of bacteria to initially break-down large protein molecules, the total concentration of nitrogen in the waste would remain high.

The present invention contains various species of Bacillus bacteria capable of this initial conversion. The Bacillus convert complex polypeptides and proteins to simple peptide chains and amino acids, thereby allowing other bacteria already present in the waste to perform ammonification.

Ammonification is the transformation of organic nitrogenous compounds to inorganic forms. This process is driven by a wide variety of microorganisms such as bacteria, actinomycetes and fungi. In soils, some organic nitrogenous compounds become resistant to biodegradation because they form complexes with phenols and/or polyphenols.

Simple proteins are mineralized to $NH^{4+}$ according to the following sequence:

An example is the transformation of urea to ammonium:

Proteins are converted to peptides or amino acids by extracellular proteolytic enzymes, such as neutral and alkaline proteases produced by Bacillus. The presence of Bacillus is crucial to the efficacy of this invention due to the fact that without the Bacillus bacteria and its extracellular proteolytic enzymes, the large complex proteins and polypeptides would not be converted to simple peptides, and subsequently amino acids, for use by naturally occurring microorganisms for the ammonification process.

Ammonium is produced following deamination (e.g. oxidative or reductive deamination) of the peptides/amino acids produced by Bacillus according to the following reactions:

Oxidative deamination:

Reductive deamination:

$NH^{4+}$ predominates in acidic and neutral environments. As pH increases, $NH_3$ predominates and is released into the atmosphere.

The next step in the nitrogen cycle process which eventually leads to denitrification, is nitrification. Nitrification is the conversion of ammonium to nitrate by microbial action. Nitrification occurs in two steps. In the first step, ammonia, produced by natural occurring microorganisms, is oxidized to nitrite. In the second step, nitrite is oxidized to nitrate. As a result of the combined activities of these bacteria, the ammonia liberated during the mineralization of organic matter is rapidly oxidized to nitrate. Thus, nitrate is the principal nitrogenous material available in soil for the growth of plants.

Conversion of ammonia to nitrite occurs via many microbes such as *Nitrosomanas europaea* and *Nitrosomanas oligicarbogenes*. These microorganisms oxidize ammonium to nitrite via hydroxylamine ($NH_2OH$). Other ammonium oxidizers are Nitrosospira, Nitrosococcus and Nitrosolobus.

The second step, conversion of nitrite to nitrate, is conducted via such microorganisms as *Nitrobacter agilis* and *Nitrobacter winogradski*. Other nitrite oxidizers are Nitrospira and Nitrococcus. Although autotrophic nitrifiers are predominant in nature, nitrification may be carried out by heterotrophic bacteria such as Arthrobacter and fungi such as Aspergillus.

After the aforementioned steps have occurred, denitrification may take place. Denitrification is a dissimilatory nitrate reduction. This process is an anaerobic respiration by which nitrate, $NO_3$ serves as an electron acceptor. $NO_3$— is eventually reduced to nitrite, $NO_2$, then to nitric oxide, NO, to nitrous oxide, $N_2O$, and subsequently nitrogen gas, $N_2$. $N_2$ gas liberation is the predominant output of denitrification.

Specifically, denitrification is carried out according to the following sequence:
$NO_3 \rightarrow NO_2 \rightarrow NO \rightarrow N_2O \rightarrow N_2$
Nitrate (Reductase) Nitrite (Reductase) Nitric Oxide (Reductase) Nitrous Oxide Nitrogen Gas There are many factors controlling denitrification in both water and soil environments. One is nitrate concentration. Nitrate serves as an electron acceptor for denitrifing bacteria and the growth rate of denitrifiers depends on the nitrate concentration.

Another factor is anoxic conditions. $O_2$ competes effectively with nitrate as a final electronic acceptor in respiration. Glucose oxidation releases more free energy in the presence of oxygen than in the presence of nitrate. Therefore, denitrification is conducted in the absence of oxygen, i.e. anaerobic conditions. However, denitrification may occur inside activated sludge floes and biofilms despite relatively high levels of oxygen in the bulk liquid. Thus, the presence of oxygen may not preclude denitrification at the microenvironment level.

The presence of organic matter is also a factor which effects denitrification because denitrifying bacteria must have an electron donor to carry out the denitrification process. There are several sources of electron donors, including raw waste and manure. The type of waste material contemplated with in the scope of this invention includes all types of mammalian waste and excretions including livestock waste, poultry waste, and organic carcasses. "Livestock" is contemplated to include any type of domesticated species, including but not limited to, cattle, pigs, sheep, horses, goats, and the like.

pH is yet another factor which controls denitrification. Denitrification is most effective at a pH between 7.0 and 8.5 with the optimum pH being approximately 7.0. Alkalinity and pH increase following denitrification.

Temperature further affects denitrification. Denitrification may occur between 35° C. and 50° C. but can also occur at low temperatures, such as 5–10° C., but at a much slower rate.

The inventive treatment composition preferably consists of a water soluble carrier, protease-producing spores and stabilized denitrifing vegetative cells.

The denitrifying species of bacteria are facultative anaerobic bacteria which produce enzymes which denitrify the waste. The bacteria grow and break down solids under aerobic and anaerobic conditions. As these facultative bacteria proliferate, the noxious odors associated with anaerobic decomposition are reduced.

The microorganisms involved in denitrification may belong to several physiological groups, such as phototrophic, organotrophic or lithotrophic microorganisms, that can switch to an anaerobic growth when nitrate is used as the electron acceptor. There are also many types of denitrifiers which belong to several taxonomic groups and can use various energy sources such as organic or inorganic chemicals or light.

Microorganisms that are capable of denitrification and are contemplated within the scope of this invention:

Pseudomonas, Bacillus, Spirilul, Hyphomicrobiun, Agrobacteriurm, Acinetobacter, Propionibacterium, Rhizobium, Corynebacterium, Cytophaga, Thiobacillus, and Alcaligene.

The most widespread genera are probably Pseudomonas (*P. fluorescent, P. aeruginosa, P. denitrificans*) and Alcaligenes.

The bacteria preferably contemplated within the scope of this invention is *Propionibacterium acidipropionic*, and preferably strain P5. However, other strains of *Propionibacterium acidipropionic* will work within the scope of this invention as long as they have the key characteristic of being able to perform denitrification.

The key enzymes produced by the P5 strain include nitrate reductase, nitrite reductase and nitrous oxide reductase. As a treatment in livestock waste, the P5 strain is applied at least $3.0 \times 10^4$ CFU/ml.

The composition of the present invention preferably contains a carrier, and, in the preferred embodiment, the carrier is water soluble. The primary function of the water soluble carrier is allowing easy dissolving upon contact with a liquid. Suitable water soluble carriers include whey and maltodextrin, such as maltodextrin M100. The water soluble carrier may consist of maltodextrin and whey in approximately a 50/50% ratio. However, any water soluble carrier is suitable within the scope of this invention.

A moisture binding agent is also useful to reduce clumping of the mixture and provide easier handling. An example of a suitable moisture binding agent is balith.

The protease-producing bacteria preferred within the scope of the invention are from the genus Bacillus. The enzymes produced by the Bacillus are neutral and alkaline proteases. When treating livestock, the Bacillus strains are applied at least $4.5 \times 10^4$ CFU/ml. The Bacillus strains present in the novel composition are preferably *Bacillus subtilis, Bacillus lichenifomrnus* and *Bacillus amyloliquefaciens*. However, any protease-producing bacteria is suitable within the scope of this invention.

The preferred percentages of the total Bacillus for each strain are approximately as follows: the *Bacillus subtilis* at approximately 10%; *Bacillus licheniformis* at approximately 20%; and *Bacillus amyloliquefaciens* at approximately 70%. The percentages in this formulation may range as follows: *Bacillus subtilis* at about 5–20%; *Bacillus lichenifornnis* at about 50–30%; and *Bacillus amyloliquefaciens at about 65–80%.

The ATCC Numbers for the bacteria are as follows: *Bacillus subtilis*, ATCC 27505; *Bacillus amyloliquefaciens*, ATCC 23842; *Bacillus lichenfomtis*, ATCC 21415; and strain P5, ATCC 55467.

The level of bacteria in the waste is critical and should be applied on a monthly basis. The bacteria should to be applied at a level of at least $3.0 \times 10^4$ CFU/ml. per strain P5 and $4.5 \times 10^4$ CFU/ml. for the total Bacillus count. These are the minimum levels that should be utilized. Higher CFU levels also work quite well, but may be cost prohibited.

The CFU or colony forming unit is the viable cell count of a sample resulting from standard microbiological plating methods. The term is derived from the fact that a single cell, when plated on appropriate medium, will grow and become a visible colony in the agar medium. Since multiple cells may give rise to one visible colony, the term colony forming unit is more correct than cell number.

Since the preferable treatment composition of the present invention contains freeze-dried bacteria cells in the form of vegetative cells and spores, it should be activated prior to use with a liquid, preferably warm water. Upon contact with warm water, the environmental conditions are suitable for growth and the endospore returns to a vegetative state. After the treatment is dissolved, it is simply poured or sprayed directly onto the waste.

Upon exposure to water, the freeze-dried bacteria germinate and the vegetative cells may reproduce. In the presence of growth supporting nutrient, such as those found in manure, the cells will enter a period of biosynthetic activity in which vegetative cellular components are produced. From this point on the bacteria proliferate in the waste environment.

The steps for the production of the specific bacterial strains of the present invention are fermentation of the bacterial strains, harvesting and freeze drying the cells and milling the freeze dried culture to a uniform size and specified activity. The fermentation is started by scaling-up a seed culture. This involves repeatedly and asceptically transferring the culture to a larger and larger volume to serve as the inoculum for the fermentation. The fermentation is carried out in large stainless steel fermentors in a medium containing proteins, carbohydrates and minerals necessary for optimal growth. After the inoculum is added to the fermentation vessel, the temperature and agitation are controlled to allow maximum growth. Once the culture reaches a maximum population density, the culture is harvested by separating the cells from the fermentation medium. This is commonly done by centrifugation. The wet cell paste is then mixed with cryoprotectants which will maintain the viability of the cells during the freezing and drying process. The mixture is then placed in trays, frozen and dried. The resulting dried cake is milled to a uniform size and plated to determine the activity. After the viable cell count has been determined, the cell count is standardized to a predetermined activity level or colony forming units per gram by blending with dry carriers.

The count of the bacteria at the time it is combined with a carrier is important. At the time of manufacture of the novel composition, the Bacillus count preferably is at least $7.9 \times 10^9$ CFU/g. The count for the *Propionibacterium acidipropionici* strain P5 preferably is at least $5.5 \times 10^9$ CFU/g. The counts may be increased from these base numbers and still have complete efficacy. The culture amounts and the carrier are added to a ribbon or paddle mixer and mixed, preferably for 15 minutes. The components must be blended enough so that uniform mixture of the carrier and cultures result. The final product is a dry flowable powder.

The preferred composition is created by combining approximately 50% whey, 49% maltodextrin M100 and 1% balith with the bacterial species of Bacillus and *Propionibacterium acidipropionci*, preferably strain P5. The Bacillus preferably utilized are *Bacillus licheniformis, Bacillus subtilis* and *Bacillus amyloliquefaciens*. The Bacillus strain preferably has a count, at application, of at least $4.5 \times 10^4$ CFU/ml. The *Propionibacterium acidipropionici* P5 strain preferably has a count, at application, of at least $3.0 \times 10^4$ CFU/ml. However, the count for Bacillus and *Propionibacterium acidipropionici* may be efficious at a count as low as $1.0 \times 10^3$ CFU/ml.

The novel composition used in both Examples 1 and 2 was produced as follows: Bacillus strains with an over blend count of $9.0 \times 10^9$ CFU/g were combined with *Propionibacterium acidipropionici* strain P5 having an over blend count of $1.1 \times 10^{10}$ CFU/g. The water soluble carriers utilized were whey at a 50% by weight content, maltodextrin M100 at a 49% by weight content and balith at approximately 1% by weight content. The total over blend count of all the bacteria of $2.0 \times 10^{10}$ CFU/g. These substances were mixed in a paddle blender for approximately 15 minutes.

The novel composition was activated with the appropriate amount of warm water prior to use in Examples 1 and 2. The application rate is dependent on the type of production facility as well as the number and type of animals.

EXAMPLE 1

Swine Lagoon Study, North Carolina Field Trial

The primary lagoons at four swine farrowing facilities were treated with the novel composition to observe the effect on crop available nitrogen, total kjeldahl nitrogen ("TKN"), ammonia, nitrates and nitrites in the waste water. Samples taken before treatment and 34 days after treatment from all lagoons indicated the novel treatment reduced the nitrogen available for first crops by 27.8%, TKN by 25% and ammonia by 54.8%. Concentrations of nitrate were reduced by 50% in three of the four lagoons. The concentration of nitrites were less than 0.01 ppm before and after treatment in all lagoons.

The following field trial documents the effects of the present invention in swine lagoon systems.

METHODS

The nitrate reducing formulation of the present invention was added to four swine lagoons at the recommended application rate (2 pounds per 1,000,000 gallons). Samples of each lagoon were taken before treatment and 34 days after treatment. The size of the lagoons and number of sows at each site are shown in Table 1.

TABLE 1

NUMBER OF SOWS AND VOLUME OF THE PRIMARY LAGOON AT EACH SITE USED IN THIS STUDY

| Site | Sows | Lagoon Volume (gallons) |
|---|---|---|
| 1 | 3,600 | 5,000,000 |
| 2 | 2,900 | 4,500,000 |
| 3 | 1,200 | 1,800,000 |
| 4 | 600 | 1,000,000 |

Samples were taken 34 days after treatment and shipped to an independent laboratory for analysis. Samples were analyzed for total kjeldahl nitrogen (TKN), nitrates, nitrites, ammonia and N, P and K values according to standard procedures.

RESULTS

The addition of the novel composition of the present invention reduced the nitrogen available for first crop by 15% to 43% in 34 days compared to the levels of available nitrogen before treatment (Table 2). The mean percent reduction of nitrogen available was 27.8%.

Figure 1:
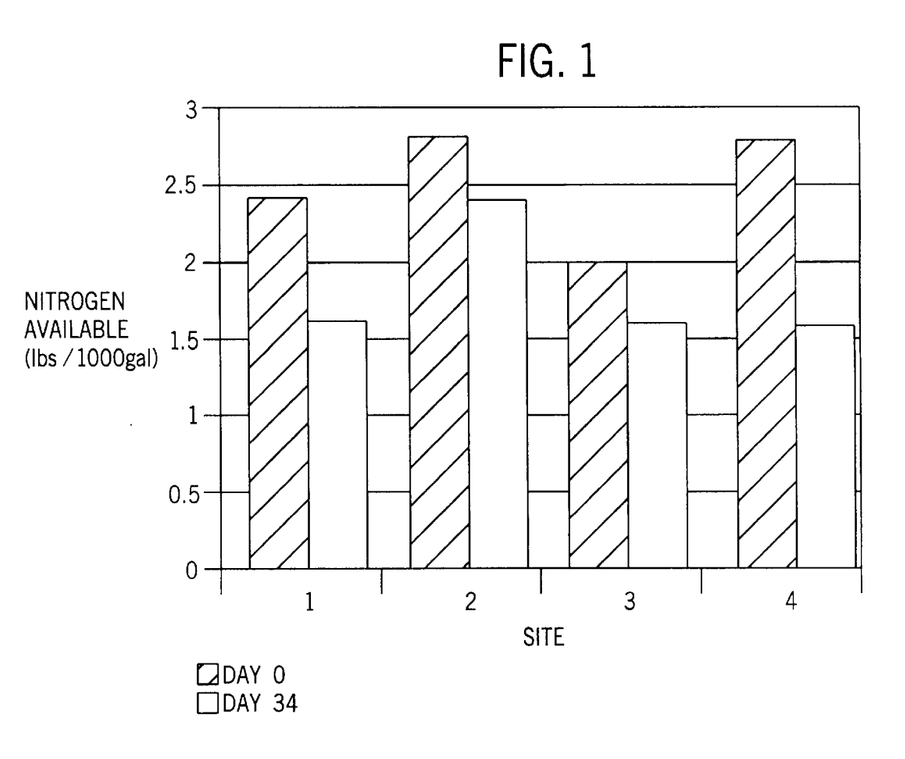
FIG. 1 is a graph illustrating the effects of the invention on nitrogen concentration available for a first crop in pounds per 1000 gallons.

FIG. 1 illustrates the effect of the novel composition on nitrogen available for the first crop. Nitrogen available for first crop are the inorganic forms of nitrogen utilized by the plants in the first year. These forms of nitrogen would include ammonia, nitrate and nitrite. Organic nitrogen must be broken down by the soil microorganisms before it is available to the crop.

TABLE 2

NITROGEN AVAILABLE FOR FIRST CROP

| | Site | | | | | | | |
|---|---|---|---|---|---|---|---|---|
| | 1 | | 2 | | 3 | | 4 | |
| Nutrients measured | Before | After | Before | After | Before | After | Before | After |
| % Nitrogen | .06 | .04 | .07 | .06 | .05 | .04 | .07 | .04 |
| Nitrogen available for first crop* (LB/1000 gallons) | 2.4 | 1.6 | 2.8 | 2.4 | 2.0 | 1.6 | 2.8 | 1.6 |
| % Change | | 33 | | 15 | | 20 | | 43 |

*Nitrogen available for first crop is based on nitrogen analysis and estimates of mineralization rates and projected loss for the application method.

TABLE 3

ANALYSIS OF TKN, NITRATE AND AMMONIA

| | Site | | | | | | | |
|---|---|---|---|---|---|---|---|---|
| | 1 | | 2 | | 3 | | 4 | |
| Analysis | Before | After | Before | After | Before | After | Before | After |
| TKN (ppm) | 538 | 350 | 788 | 615 | 589 | 538 | 792 | 523 |
| % Change in TKN | | 35 | | 22 | | 9 | | 34 |
| Nitrate nitrogen, ppm | 0.4 | 0.2 | 0.2 | 0.1 | 0.4 | 0.2 | 0.1 | 0.2 |
| % Change in nitrate | | 50 | | 50 | | 50 | | +50 |
| Ammonia nitrogen, ppm | 520 | 250 | 600 | 210 | 470 | 215 | 575 | 310 |
| % Change in Ammonia | | 52 | | 65 | | 56 | | 46 |

Figure 2:
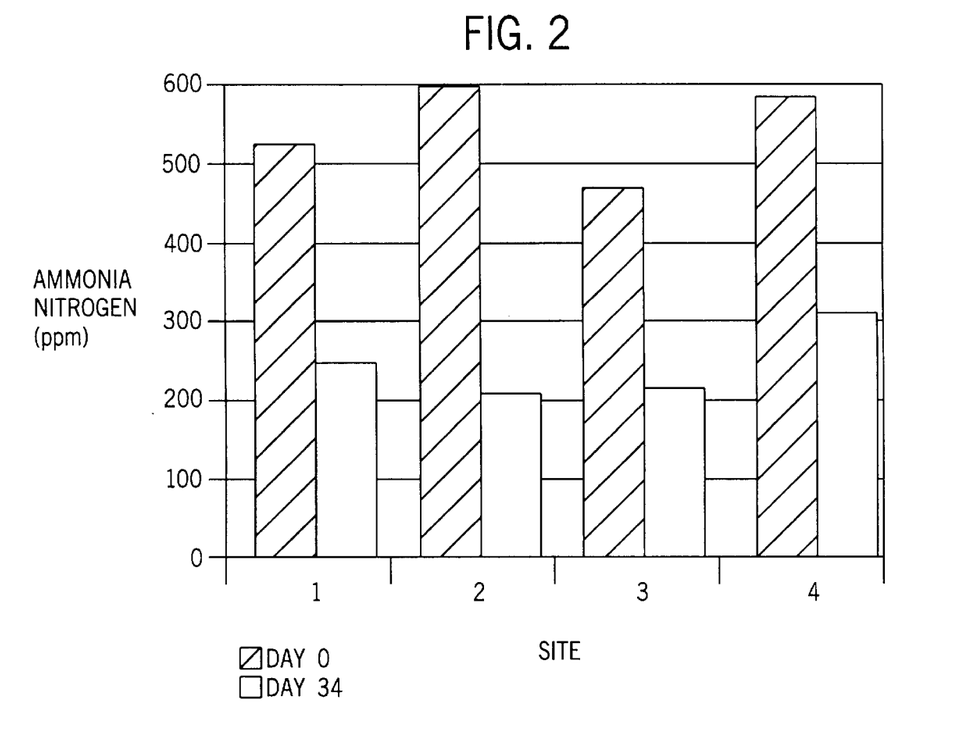
FIG. 2 is a graph illustrating the effect of the invention on ammonia nitrogen concentration in parts per million.

The novel composition reduced TKN and ammonia concentrations in all lagoons and nitrate concentrations in three of the four lagoons (FIG. 2 and Table 3). The nitrite concentration in all lagoons was less than 0.01 ppm.

The treatment of the manure with the present invention reduces TKN, ammonia, nitrates and decreases the nitrogen available for first crop.

Table 4 illustrates the application rate guide followed for Example 1.

TABLE 4

| Nursery pigs | 0.5 pound/500 head |
|---|---|
| Finishing pigs | 1.0 pound/500 head |
| Gestating sows | 1.0 pound/500 head |
| Sows and litters | 2.0 pounds/500 head |

EXAMPLE 2

Swine Lagoon Study, North Carolina Field Trial

SITE DESCRIPTION

The field trial was conducted at two sites in Bladen County, North Carolina. Each site consisted of eight finishing barns each containing 720 hogs. Manure from all barns at each site was collected in shallow pits and drained to a single-stage, anaerobic lagoon by gravity through plugs pulled on a rotating basis. All pits were recharged with recycled lagoon liquid. The lagoon at each site contained approximately 9.0 million gallons.

METHODS

Treatment: The novel composition was added to the single-stage, anaerobic lagoon at one site at the recommended application rate (2 pounds per 1,000,000 gallons) at the start of the trial (Apr. 10, 1996). The monthly maintenance formula of the novel composition was added to each barn at the recommended application rate of 1 lb. per 500 head of finishing pigs. The lagoon and barns at the other site were not treated and served as the control for this field trial.

Sampling: Samples were collected monthly from the treated lagoon over a 12 month period (Aug. 10, 1996–Mar. 21, 1997). The control lagoon was sampled periodically. At each sampling day, vertical cross-sectional samples of the entire depth of a lagoon were collected from five locations in the lagoon. The sampling sites were located in the lagoon by east-west and north-south landmarks on the berm. Samples were collected from the lagoon using a 15 foot long, hollow, PVC tube (1.0 inch in diameter) fitted with a stopper at one end. The stopper was connected to a handle at the other end of the sampling tube via a metal rod running the length of the sampling tube. The sampling tube, with the stopper in the open position, was slowly lowered vertically down into the lagoon until the tube reached the bottom. At the bottom, the stopper was pulled into the tube via the handle to trap the column of solids and liquid in the sampling tube. The total sample was collected by slowly releasing the stopper from the bottom of the tube. The sample of solids and liquid was collected in 1 liter plastic containers that held an amount of sample approximately equal to 4–5 feet of depth. All samples were labeled by the location and depth and stored on ice until chemical and microbiological analyses.

In addition to obtaining cross-sectional lagoon samples, a composite surface sample (1 foot below the surface) was collected. The visual activity and odor level of the lagoon was also recorded at each sampling date.

Liquid samples were shipped to AgTech Product Inc.'s laboratory packed on cold packs. Samples were analyzed for microbiological activity using standard enumeration procedures. Total solids, total nitrogen (TKN) and dissolved ammonia were determined using standard AOAC procedures at an independent commercial laboratory.

RESULTS

Figure 3:
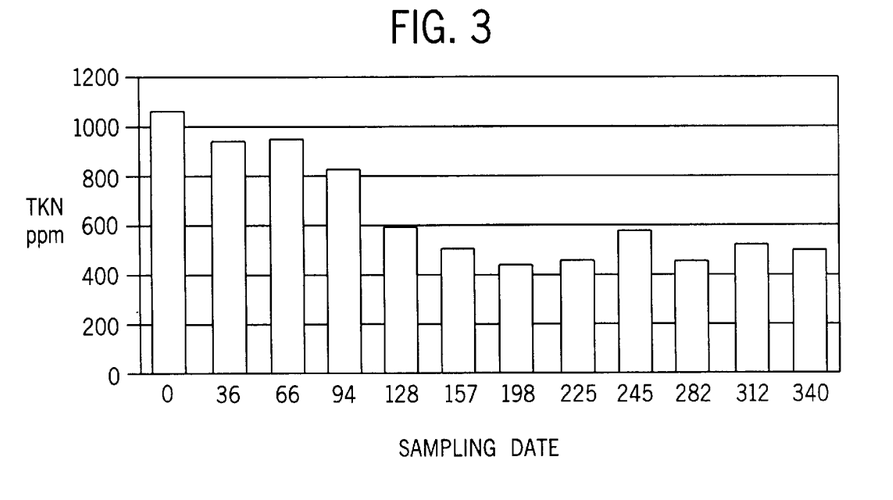
FIG. 3 is a graph illustrating total nitrogen content of a lagoon following treatment utilizing the present invention in parts per million.

The total nitrogen content of samples taken from the treated lagoon before and every month after treatment for one year are shown in FIG. 3. The values are averages of three sample locations collected from the top 4–5 feet of the lagoon at each sampling day. The total nitrogen content of the lagoon decreased throughout the entire sampling period. Some reduction in total nitrogen would be expected in the summer months when the microbiological activity increases due to warmer temperatures. However, the total nitrogen levels in the treated lagoon did not increase as expected in the fall and winter when microbiological activity would be lower.

To confirm these results were the effect of the novel composition, the untreated (control) lagoon was sampled. These results are similar to other studies conducted in North Carolina where the addition of this novel composition reduced the total nitrogen by an additional 30% to 48%.

In addition to the reduction in total nitrogen, cross sectional sampling of the treated lagoon over the first six months indicated that the total solids were reduced by 64%.

I claim:

1. A biological waste treatment composition comprising:
    denitrifying bacteria, said denitrifying bacteria are *Propionibacterium acidipropionici* having an activity of at least approximately $3.0 \times 10^4$ CFU/ml;
    protease-producing bacteria, said protease-producing bacteria are from the genus Bacillus and are selected from the group consisting of *Bacillus subtilis, Bacillus licheniformis* and *Bacillus amyloliguefaciens* and have an activity of at least approximately $4.5 \times 10^4$ CFU/ml; and
    a carrier.

2. The composition of claim 1 wherein said *Propionibacterium acidipropionici* is strain P5.

3. The composition of claim 1 wherein said carrier is a water soluble carrier.

4. The composition of claim 3 which further contains a moisture binding agent and said water soluble carrier is selected from the group consisting of whey, maltodextrin, and a mixture thereof.

5. The composition of claim 4 wherein said moisture binding agent is balith.

6. The composition of claim 1 wherein said Propionibacterium has an activity of at least approximately $5.5 \times 10^9$ CFU/ml.

7. The composition of claim 1 wherein said Bacillus has an activity of at least approximately $7.9 \times 10^9$ CFU/ml.

8. The composition of claim 1 wherein said Bacillus are present in a ratio of *Bacillus subtilis* at 10%, *Bacillus licheniformis* at 20% and *Bacillus amyloliquefaciens* at 70%.

9. The composition of claim 4 wherein said water soluble carrier consists of approximately 50% by weight maltodextrin and approximately 50% by weight whey.

10. The composition of claim 4 wherein said maltodextrin is present in a range of approximately 40–60% by weight and said whey is present in a range of approxiately 40–60% by weight.

11. The composition of claim 5 wherein said whey is present at approximately 50% by weight, said maltodextrin is present at approximately 49% by weight and said balith is present at approximately 1% by weight.

12. The composition of claim 1 wherein said Bacillus is in the form of spores and said Propionibacterium is in the form of vegetative cells.

13. A method for reducing the nitrogen concentration in a biological nitrogen containing material comprising:
    combining denitrifying bacteria, said denitrifying bacteria are *Propionibacterium acidipropionici* having an activity of at least approximately $3.0 \times 10^4$ CFU/ml and protease-producing bacteria, said protease-producing bacteria are from the genus Bacillus and are selected from the group consisting of *Bacillus subtilis, Bacillus licheniformis* and *Bacillus amyloliquefaciens* and have an activity of at least approximately $4.5 \times 10^4$ CFU/ml to form a mixture; and
    applying said mixture onto a biological nitrogen containing material.

14. The method of claim 13 wherein said biological nitrogen containing materialontains livestock waste.

15. The method of claim 13 wherein said mixture further contains a water soluble carrier.

16. The method of claim 15 wherein said mixture is dissolved in water prior to applying said mixture onto said material.

17. The method of claim 13 wherein said *Propionibacterium acidipropionici* is strain P5.

18. The method of claim 15 wherein said water soluble carrier is selected from the group consisting of maltodextrin, whey, and a combination thereof; and wherein said mixture further contains a moisture binding agent.

19. A method for reducing the nitrogen concentration in a biological nitrogen containing material comprising:

providing a protease-producing bacteria, said protease-producing bacteria are from the genus Bacillus and are selected from the group consisting of *Bacillus subtilis, Bacillus licheniformis* and *Bacillus amyloliquefaciens* and have an activity of at least approximately $4.5 \times 10^4$ CFU/ml;

applying said protease-producing bacteria to the biological nitrogen containing material;

providing a denitrifying bacteria, said denitrifying bacteria are *Propionibacterium acidipropionici* having an activity of at least approximately $3.0 \times 10^4$ CFU/ml; and applying said denitrifying bacteria to said biological nitrogen containing material.

20. The method of claim 19 wherein said protease-producing bacteria and said denitrifying bacteria are applied simultaneously.

21. A method of producing a mixture able to reduce nitrogen levels in nitrogen containing material consisting of:

combining a denitrifying bacteria, said denitrifying bacteria are *Propionibacterium acidipropionici* having an activity of at least $5.5 \times 10^9$ CFU/g with a protease-producing bacteria said protease-producing bacteria are from the genus Bacillus and are selected from the group consisting of *Bacillus subtilis, Bacillus licheniformis* and *Bacillus amyloliguefaciens* having an activity of at least $7.9 \times 10^9$ CFU/g and a water soluble carrier.

22. The method of claim 21 wherein said *Propionibacterium acidipropionici* is strain P5.

23. The method of claim 21 wherein said carrier is selected from the group consisting of maltodextrin, whey, and a combination thereof.

* * * * *

UNITED STATES PATENT AND TRADEMARK OFFICE
CERTIFICATE OF CORRECTION

PATENT NO.     : 6,221,650 B1
DATED          : April 24, 2001
INVENTOR(S)    : Thomas G. Rehberger It is certified that error appears in the above-identified patent and that said Letters Patent is hereby corrected as shown below:

<u>Title page,</u>
Item [56], References Cited, under OTHER PUBLICATIONS,
Schmidt et al, delete "University," at the end of the first line and beginning of the second line <u>Column 12,</u>
Line 54, delete "materialontains" and substitute therefore -- material contains --.

Signed and Sealed this

Twenty-third Day of July, 2002

Attest:

Attesting Officer

JAMES E. ROGAN
Director of the United States Patent and Trademark Office